United States Patent
Bai et al.

(10) Patent No.: US 11,654,421 B2
(45) Date of Patent: May 23, 2023

(54) METAL CATALYSTS WITH LOW-ALKALI METAL CONTENT AND ACID/METAL BIFUNCTIONAL CATALYST SYSTEMS THEREOF

(71) Applicant: ExxonMobil Technology and Engineering Company, Annandale, NJ (US)

(72) Inventors: Chuansheng Bai, Phillipsburg, NJ (US); Majosefina Cunningham, Whitehall, PA (US); Jihad M. Dakka, Whitehouse Station, NJ (US); Preeti Kamakoti, Berkeley Heights, NJ (US); Aruna Ramkrishnan, Bridgewater, NJ (US); Anjaneya S. Kovvali, Herndon, VA (US); Anita S. Lee, Spring, TX (US)

(73) Assignee: EXXONMOBIL TECHNOLOGY AND ENGINEERING COMPANY, Annandale, NJ (US)

( * ) Notice: Subject to any disclaimer, the term of this patent is extended or adjusted under 35 U.S.C. 154(b) by 266 days.

(21) Appl. No.: 16/947,701

(22) Filed: Aug. 13, 2020

(65) Prior Publication Data

US 2021/0046461 A1 Feb. 18, 2021

Related U.S. Application Data

(60) Provisional application No. 62/886,985, filed on Aug. 15, 2019.

(51) Int. Cl.
*B01J 23/80* (2006.01)
*C07C 41/01* (2006.01)
(Continued)

(52) U.S. Cl.
CPC ............... *B01J 23/80* (2013.01); *B01J 21/18* (2013.01); *B01J 35/0013* (2013.01);
(Continued)

(58) Field of Classification Search
CPC ...... B01J 23/80; B01J 35/0013; B01J 35/023; B01J 35/026; B01J 35/1014;
(Continued)

(56) References Cited

U.S. PATENT DOCUMENTS

| | | |
|---|---|---|
| 4,423,155 A | 12/1983 | Bell et al. |
| 5,218,003 A | 6/1993 | Lewnard et al. |

(Continued)

FOREIGN PATENT DOCUMENTS

| | | | | |
|---|---|---|---|---|
| CN | 101485983 A | | 7/2009 | |
| CN | 104646049 | * | 5/2015 | ............. B01J 23/80 |

(Continued)

OTHER PUBLICATIONS

M. Gentzen et al.; "Bifunctional hybrid catalysts derived from Cu/Zn-based nanoparticles for single-step dimethyl ether synthesis." Catalysis Science & Technology, 6, pp. 1054-1063. (Year: 2016).*

(Continued)

*Primary Examiner* — Patricia L. Hailey
(74) *Attorney, Agent, or Firm* — Shook, Hardy & Bacon L.L.P.

(57) ABSTRACT

Methods of producing metal catalysts can include mixing two or more metal salts and an aluminum salt in water to produce a metal catalyst precursor solution; mixing the metal catalyst precursor solution and an alkali metal buffer solution to produce a precipitate; ion exchanging the alkali metal in the precipitate for a non-alkali cation to produce a low-alkali metal precipitate comprising 3 wt % or less alkali metal by weight of the precipitate on a dry basis; producing (Continued)

a powder from the low-alkali metal precipitate; and calcining the powder to produce a metal catalyst. Such metal catalysts may be useful in producing bifunctional catalyst systems that are useful in, among other things, converting syngas to dimethyl ether in a single reactor.

27 Claims, 6 Drawing Sheets

(51) Int. Cl.
| | |
|---|---|
| B01J 37/04 | (2006.01) |
| B01J 37/03 | (2006.01) |
| B01J 37/30 | (2006.01) |
| B01J 37/00 | (2006.01) |
| B01J 37/08 | (2006.01) |
| B01J 37/34 | (2006.01) |
| B01J 37/06 | (2006.01) |
| B01J 37/02 | (2006.01) |
| B01J 37/18 | (2006.01) |
| B01J 35/00 | (2006.01) |
| B01J 35/02 | (2006.01) |
| B01J 35/10 | (2006.01) |
| B01J 21/18 | (2006.01) |

(52) U.S. Cl.
CPC ......... *B01J 35/026* (2013.01); *B01J 35/1014* (2013.01); *B01J 35/1019* (2013.01); *B01J 35/1038* (2013.01); *B01J 35/1042* (2013.01); *B01J 35/1047* (2013.01); *B01J 35/1061* (2013.01); *B01J 37/0036* (2013.01); *B01J 37/0236* (2013.01); *B01J 37/031* (2013.01); *B01J 37/04* (2013.01); *B01J 37/06* (2013.01); *B01J 37/088* (2013.01); *B01J 37/18* (2013.01); *B01J 37/30* (2013.01); *B01J 37/348* (2013.01); *C07C 41/01* (2013.01)

(58) Field of Classification Search
CPC ................ B01J 35/1019; B01J 35/1038; B01J 35/1072; B01J 35/1047; B01J 37/1061; B01J 35/1066; B01J 37/0018; B01J 37/0036; B01J 37/0236; B01J 37/031; B01J 37/04; B01J 37/06; B01J 37/088; B01J 37/18; B01J 37/30; B01J 37/348; B01J 38/74; C01P 2004/61; C01P 2004/90; C01P 2006/14; C01P 2006/16
USPC ....... 502/104, 302, 305, 308, 312, 313, 317, 502/320, 323–327, 330, 332, 346, 348, 502/351, 355
See application file for complete search history.

(56) References Cited

U.S. PATENT DOCUMENTS

| | | | |
|---|---|---|---|
| 6,069,107 | A | 5/2000 | Kuznetsov et al. |
| 2012/0157554 | A1 | 6/2012 | Okuyama et al. |
| 2013/0030224 | A1* | 1/2013 | Kim ..................... B01J 23/74 |
| | | | 568/885 |
| 2013/0211147 | A1 | 8/2013 | Cheiky et al. |
| 2016/0347906 | A1 | 12/2016 | Williams et al. |
| 2017/0297986 | A1 | 10/2017 | Lee et al. |

FOREIGN PATENT DOCUMENTS

| | | | | |
|---|---|---|---|---|
| CN | 104646049 | A | | 5/2015 |
| CN | 104069856 | B | * | 4/2016 |
| CN | 106536045 | A | | 3/2017 |
| JP | 2003-38957 | A | | 2/2003 |
| WO | WO-2005046855 | A2 | * | 5/2005 ............... B01J 21/12 |

OTHER PUBLICATIONS

M. Gentzen et al., "Bifunctional catalysts based on colloidal Cu/Zn nanoparticles for the direct conversion of synthesis gas to dimethyl ether and hydrocarbons." Applied Catalysis A, General 557, pp. 99-107. (Year: 2018).*

Hiroyuki Kamata et al., "Steam Reforming of Dimethyl Ether over Cu/ZnO/ZrO2 and $\gamma$—Al2O3 Mixed Catalyst Prepared by Extrusion." Journal of the Japan Petroleum Institute, 51, 3, pp. 157-164. (Year: 2008).*

Bae, J.-W., et al., "Coproduction of Methanol and Dimethyl Ether from Biomass-Derived Syngas on a Cu—ZnO—Al2O3/$\gamma$—Al2O3 Hybrid Catalyst", Energy and Fuels, vol. 22, No. 1, pp. 223-230 (2008).

Zhang, Q., et al., "Improvement of a Mesh-Type Cu/Ni/$\gamma$—Al2O3/Al Catalyst for Steam Reforming of Dimethyl Ether by Metal (Fe, Zn or La) Addition for CO in Situ Removal", Modern Research in Catalysis, vol. 7, pp. 1-16 (Jan. 31, 2018).

Non-Final Office Action dated Apr. 11, 2022 in U.S. Appl. No. 16/993,219, 12 pages.

Non-Final Office Action dated Jul. 21, 2022 in U.S. Appl. No. 16/947,699, 12 pages.

Non-Final Office Action dated Aug. 4, 2022 in U.S. Appl. No. 16/947,704, 14 pages.

Non-Final Office Action dated Sep. 15, 2022 in U.S. Appl. No. 16/947,706, 8 pages.

Notice of Allowance dated Oct. 21, 2022 in U.S. Appl. No. 16/993,219, 9 pages.

Final Office Action dated Jan. 12, 2023 in U.S. Appl. No. 16/947,704, 16 pages.

\* cited by examiner

METAL CATALYSTS WITH LOW-ALKALI METAL CONTENT AND ACID/METAL BIFUNCTIONAL CATALYST SYSTEMS THEREOF

CROSS REFERENCE TO RELATED APPLICATION

This application claims priority to U. S. Provisional Application Ser. No. 62/886,985 filed Aug. 15, 2019, which is herein incorporated by reference in its entirety.

FIELD

The present disclosure relates to catalysts for direct conversion of syngas to dimethyl ether.

BACKGROUND

Various processes have been proposed for producing dimethyl ether from natural gas. One such process involves co-feeding natural gas with an enriched oxygen stream to an autothermal reformer to produce syngas. Dimethyl ether may then be produced in a two-stage process. In a first stage, methanol is synthesized from the syngas. In the methanol synthesis step, un-reacted gas from the methanol synthesis reactor may be recycled back to the reactor, thereby acting as a syngas quench cooler. The recycle ratio (recycle gas to syngas feed gas) can be quite high in commercial practice, such as from 3:1 to 7:1, due to equilibrium limitations in methanol conversion. In the second stage, methanol is fed to a dimethyl ether reactor where dimethyl ether and water are produced. Water is separated from dimethyl ether is a subsequent stage.

Air separation (for providing an enriched oxygen feed), autothermal reforming, and substantial internal product recycle imposes significant operating and equipment costs for conventional systems for producing dimethyl ether from natural gas. It would therefore be desirable to provide new integrated processes for the production of dimethyl ether from natural gas.

A newer method has been developed for a one-stage process of converting syngas to dimethyl ether. The newer method uses two separate catalysts in a single reactor to convert CO and $H_2$ to methanol with a metal catalyst and the methanol to dimethyl ether with an acid second catalyst. However, the two catalysts being present together and mixed causes catalyst deactivation over time. For example, the acid catalysts produce coke that deactivates the metal catalysts. Further, the metal from the catalysts tends to migrate under reaction conditions preferentially to the acid sites of the acid catalysts and poison or deactivate the acid portion of the bifunctional catalyst.

SUMMARY

The present disclosure relates to methods of producing metal catalysts and bifunctional catalyst systems comprising said metal catalysts. The metal catalysts described herein have low alkali-metal concentrations, which reduces the metal migration in the acid/metal bifunctional catalyst systems that tend to deactivate the acid catalyst component.

The present disclosure includes a method comprising: mixing two or more metal salts and an aluminum salt in water to produce a metal catalyst precursor solution; mixing the metal catalyst precursor solution and an alkali metal buffer solution to produce a precipitate; ion exchanging the alkali metal in the precipitate for a non-alkali cation to produce a low-alkali metal precipitate comprising 3 wt % or less alkali metal by weight of the precipitate on a dry basis; producing a powder from the low-alkali metal precipitate; and calcining the powder to produce a metal catalyst.

The present disclosure also includes a metal catalyst produced according to the preceding method.

The present disclosure also includes an acid/metal bifunctional catalyst system comprising the metal catalyst produced according to the preceding method and an acid catalyst. Such acid/metal bifunctional catalyst system can be prepared by dry mixing, extrusion methods, or slurry mixing.

BRIEF DESCRIPTION OF THE DRAWINGS

The following figures are included to illustrate certain aspects of the embodiments, and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION

The present disclosure relates to methods of producing metal catalysts and bifunctional catalyst systems comprising said metal catalysts. The metal catalysts described herein have low alkali-metal concentrations, which reduces the metal migration in the acid/metal bifunctional catalyst systems that tend to deactivate the acid catalyst component.

Metal Catalysts having a Low Alkali-Metal Content and Resultant Acid/Metal Bifunctional Catalyst Systems The metal catalysts of the present disclosure are produced in using an alkali metal buffer solution. However, alkali metals in a resultant metal catalyst deactivate the catalyst. Accordingly, the methods further include an ion exchange step to reduce the concentration of the alkali metal in the final metal catalyst composition.

Figure 1:
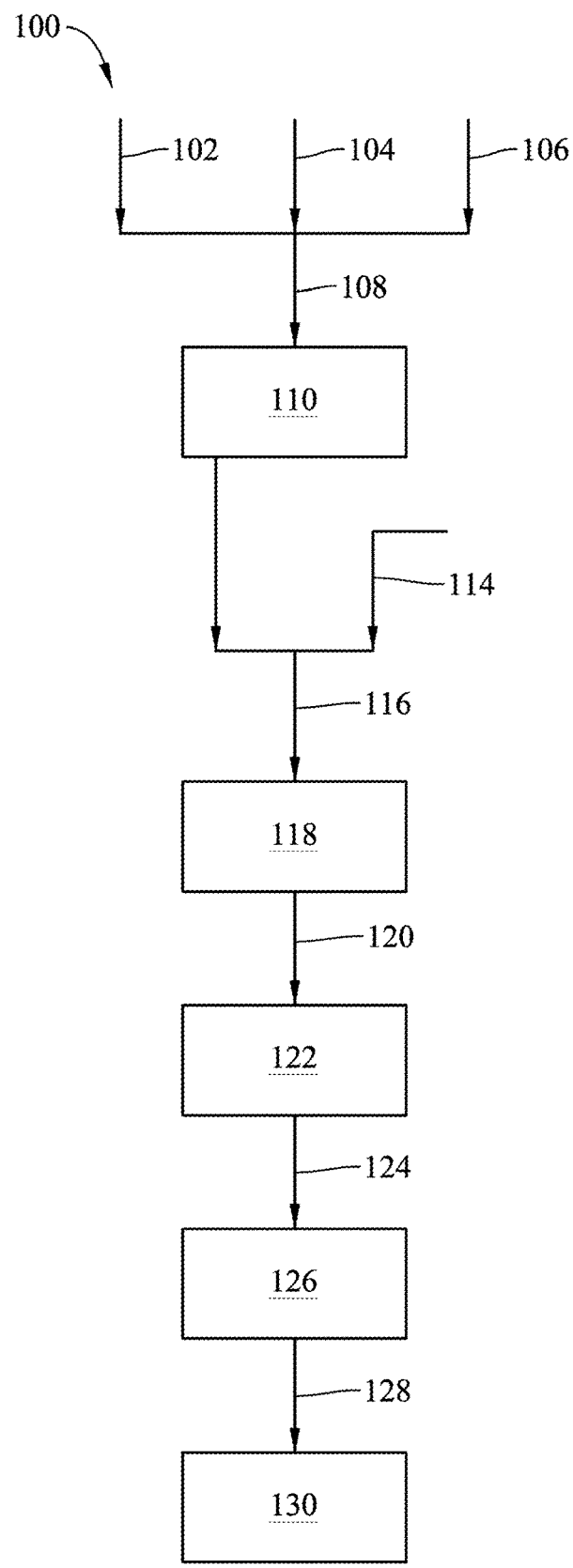
FIG. 1 is a flowchart illustrating an example method of preparing metal catalysts described herein with low alkali-metal concentrations.

FIG. 1 is a flowchart illustrating an example method 100 of preparing a metal catalyst. The method includes mixing 108 two or more metal salts (illustrated as first metal salt 102 and a second metal salt 104) and an aluminum salt 106 in water to produce a metal catalyst precursor solution 110. The salts 102, 104, 106 can, individually or in any combination, be dispersed in the water before mixing. Alternatively, one or more can be dispersed in the water and then the remaining salts can be added.

The method 100 then includes mixing 116 the metal catalyst precursor solution 110 with an alkali buffer solution 114, which produces a precipitate 118.

The first metal salt 102 can be a salt of a first metal selected from the group consisting of Cu, Cr, Ag, Au, Ru, Rh, Pd, Re, Os, Ir, and Pt, and a second metal salt 104 can be a salt of a second metal selected from the group consisting of Ti, V, Cr, Mn, Fe, Co, Ni, Zn, a rare earth metal, a La series metal, and a Y series metal. The metal catalyst precursor solution 110 can include one or more of the first metal salts 102 and one or more of the second metal salts 104.

The metal salts 102 and 104 and the aluminum salt 106 can be metal or aluminum salts with a counter ion selected from the group consisting of fluoride, chloride, bromide, acetate, carbonate, citrate, nitrate, nitrite, phosphate, sulfate, and the like. One skilled in the art will recognize the correct metal salts 102 and 104 and the aluminum salt 106 to use to cause a precipitate of the metals and aluminum to form.

The alkali buffer solution 114 can be a buffer of pH about 6.5 to about 8.0 (or about 7.0 to about 8.0, or about 7.2 to about 7.6) using sodium and/or potassium components. An example buffer is a 1.0 M solution of $KH_2PO_4$—$K_2HPO_4$ having a pH of 7.4.

Optionally, the metal catalyst precursor solution 110 and/or an alkali buffer solution 114 may be at an elevated temperature (e.g., about 40° C. to about 90° C., or about 50° C. to about 85° C., or about 60° C. to about 80° C.) before mixing.

The mixture of the metal catalyst precursor solution 110 and an alkali buffer solution 114 may be aged at an room temperature or an elevated temperature (e.g., about 25° C. to about 90° C., or about 40° C. to about 85° C., or about 60° C. to about 80° C.) for a sufficient amount of time (e.g., 5 minutes to 24 hours, or 15 minutes to 12 hours, or 30 minutes to 6 hours) to produce a desired amount of the precipitate 118.

The method 100 then includes ion exchanging 120 the alkali metal in the precipitate 118 for a non-alkali cation to produce a low-alkali metal precipitate 122 comprising 3 wt % or less (e.g., 0.1 wt % to 3 wt %, or 0.5 wt % to 3 wt %, or 0.1 wt % to 1 wt %, or 1 wt % to 3 wt %) potassium by weight of the precipitate on a dry basis.

Ion exchange 120 can be performed via any suitable method including, but not limited to, contacting the precipitate 118 with the non-alkali cation, dialysis methods, electrolytic ion exchange methods, and the like.

The non-alkali cation solutions can be acid or salts and, for example, include a cation selected from the group consisting of hydrogen, ammonium, and the like and an anion selected from the group consisting of fluoride, chloride, bromide, acetate, carbonate, bicarbonate, citrate, nitrate, nitrite, phosphate, sulfate, and the like (e.g., ammonium nitrate or hydrochloric acid).

Ion exchange 120 can be performed at a room temperature or an elevated temperature (e.g., about 25° C. to about 90° C., or about 40° C. to about 85° C., or about 60° C. to about 80° C.) for a sufficient amount of time (e.g., about 5 minutes to about 24 hours, or about 15 minutes to about 12 hours, or about 30 minutes to about 6 hours) to produce a desired amount of the precipitate 118. Further, the ion exchange 120 step can be performed more than once to further reduce the alkali-metal concentration.

Optionally, before performing ion exchange 120, the precipitate 118 can be washed (e.g., with water), dried (e.g., at about 25° C. to about 90° C. for about 5 minutes to about 24 hours), and/or ground. Grinding may increase the surface area of the precipitate 118 and hasten ion exchange 120.

After the low-alkali metal precipitate 122 is formed, the method 100 can include producing 124 a powder 126 from the low-alkali metal precipitate 122. Producing 124 the powder 126 can include washing (e.g., with water), drying (e.g., at about 25° C. to about 90° C. for about 5 minutes to about 24 hours), and/or grinding the low-alkali metal precipitate 122.

Once the powder 126 is produced, the method 100 includes calcining 128 the powder 126 to produce a metal catalyst 130. Calcining 128 may occur in an oxygen-containing gas (e.g., oxygen, air, oxygen-enriched air, and the like) at a temperature of about 200° C. to about 400° C. (or about 250° C. to about 350° C., or about 275° C. to about 375° C.) for any suitable amount of time (e.g., about 10 minutes to about 48 hours, or about 30 minutes to about 24 hours, or about 1 hour to about 12 hours, or about 1 hour to about 6 hours).

Preferably, the powder 126 comprises the water at about 5 wt % or less (or 0 wt % to about 5 wt %, or 0 wt % to about 3 wt %, or about 0.1 wt % to about 3 wt %, or 0 wt % to about 1 wt %).

The produced metal catalyst 130 can have an alkali metal content of about 3 wt % or less (or 0.5 wt % to 3 wt %, or 0.5 wt % to 2.5 wt %, or 1 wt % to 2 wt %, or 1 wt % to 1.5 wt %, or 0.5 wt % to 1.5 wt %) as determined by X-ray fluorescence.

The metal catalyst 130 should be suitable for converting CO and $H_2$ to methanol. Examples of metal catalysts 130 can include, but are not limited to, a M1/M2/Al catalyst, wherein M1 is selected from the group consisting of Cu, Cr, Ag, Au, Ru, Rh, Pd, Re, Os, Ir, Pt, and any combination thereof, wherein M2 is selected from the group consisting of Ti, V, Cr, Mn, Fe, Co, Ni, Zn, a rare earth metal, a La series metal, a Y series metal, and any combination thereof, and wherein M1 and M2 are different.

The metal catalyst 130 may have an average diameter (determined by light scattering) of about 0.01 μm to about 10 μm, or about 0.01 μm to about 1 μm, or about 0.1 μm to about 2 μm, or about 1 μm to about 5 μm, or about 2 μm to about 10 μm.

The metal catalyst 130 particles may have a $N_2$ BET surface area according to ASTM D3663-03 (2015) of about 40 $m^2$/g to about 200 $m^2$/g (about 45 $m^2$/g to about 150 $m^2$/g, or about 50 $m^2$/g to about 100 $m^2$/g).

The metal catalyst 130 particles may have an average pore volume according to $N_2$ BET about 0.1 mL/g to about 0.4 mL/g (or about 0.15 mL/g to about 0.35 mL/g, or about 0.2 mL/g to about 0.3 mL/g).

The metal catalyst 130 particles may have an average pore size according to ASTM D4641-17 of about 5 nm to about 25 nm (or about 10 nm to about 25 nm, or about 15 nm to about 20 nm).

A metal catalyst described herein can then be wet or dry mixed with an acid catalyst and optionally inert particles to produce an acid/metal bifunctional catalyst system suitable for, among other things, converting syngas to dimethyl ether in a single reactor. Optionally, the mixture can further include binders and be extruded to form the acid/metal bifunctional catalyst system.

By way of nonlimiting example, an acid/metal bifunctional catalyst system can be formed by dry admixing a metal catalyst described herein, an acid catalyst, and optionally inert particles.

In another nonlimiting example, an acid/metal bifunctional catalyst system can be formed by mixing the metal catalyst described herein with an acid catalyst and a binder to form a dough; and extruding the dough to produce an acid/metal bifunctional catalyst system. Said acid/metal bifunctional catalyst system can be used as extruded or optionally dried (e.g., at about 25° C. to about 90° C. for about 5 minutes to about 24 hours), calcined (e.g., as described above), ground, or any combination thereof. Examples of binders include, but are not limited to, clay, theta-alumina, delta-alumina, alpha-alumina, silica, titania, zirconia, boric acid, carbon, organic compounds (e.g., polymers), and the like, and any combination thereof).

In another nonlimiting example, an acid/metal bifunctional catalyst system can be formed by mixing the metal catalyst described herein with an acid catalyst and a solvent to form a slurry; heating the slurry; and drying the slurry to produce an acid/metal bifunctional catalyst system. Said acid/metal bifunctional catalyst system can be used as extruded or optionally dried (e.g., at about 25° C. to about 90° C. for about 5 minutes to about 24 hours), calcined (e.g., as described above), ground, or any combination thereof. Examples of solvents include, but are not limited to, water, methanol, ethanol, alcohols of $C_1$ to $C_{10}$, oxygenates, and the like, and any combination thereof.

The acid catalyst may be any acid catalyst suitable for converting methanol to dimethyl ether. Generally, the acid property of the acid catalyst may be Lewis acidity, Bronsted acidity, or the combination of the both Lewis acidity and Bronsted acidity. Examples of acid catalysts can include, but are not limited to, a zeolite, an ion exchanged zeolite, molecular sieves (e.g., SAPO), metal oxides (e.g., oxides of aluminum, silicon, zirconium, boron, and combinations thereof like alumiosilicates, boroaluminosilicates, borosilicates, and the like), and any combination thereof. Examples of zeolites can include, but are not limited to, MCM-49, HZSM-5-5B, mordenite, ZSM-35, ZSM-48, ZSM-11, Chabazite, boric acid modified alumina, phosphorus oxide modified alumina, ERS-8, MoPOx, and the like, and any combination thereof. Examples of combinations of acid catalyst include, but are not limited to, $WO_3$, $ZrO_2$, $SiO_2$, resins, metal organic frameworks (MOFs), zeolite imidazolate frameworks (ZIFs), and the like, and any combination thereof.

The acid catalyst may have an average diameter (determined by light scattering) of about 1 μm to about 100 μm, or about 1 μm to about 25 μm, or about 20 μm to about 50 μm, or about 25 μm to about 75 μm, or about 50 μm to about 100 μm.

The metal catalyst component may be present in the acid/metal bifunctional catalyst system at about 10 wt % or greater (or about 10 wt % to 80 wt %, or 10 wt % to 25 wt %, or 25 wt % to 50 wt %, or 50 wt % to 80 wt %) based on the total weight of the acid/metal bifunctional catalyst system. The acid catalyst component may be present in the acid/metal bifunctional catalyst system at about 10 wt % or greater (or about 10 wt % to 80 wt %, or 10 wt % to 25 wt %, or 25 wt % to 50 wt %, or 50 wt % to 80 wt %) based on the total weight of the acid/metal bifunctional catalyst system. When present, the inert particles may be present in the acid/metal bifunctional catalyst system at about 5 wt % or greater (or about 5 wt % to 80 wt %, or 10 wt % to 25 wt %, or 25 wt % to 50 wt %, or 50 wt % to 80 wt %) based on the total weight of the acid/metal bifunctional catalyst system.

A weight ratio of acid catalyst component to metal catalyst component in the acid/metal bifunctional catalyst system can be about 2:1 to about 1:10, or about 1.5:1 to about 1:5, or about 1:1 to about 1:4.

The acidity of the acid/metal bifunctional catalyst system measured with pyridine for Bronsted acid cites (1545 $cm^{-1}$ and 1450 $cm^{-1}$ infrared spectra bands) and ammonia for Lewis acid cites (1620 $cm^{-1}$ and 1450 $cm^{-1}$ infrared spectra bands) may be cumulatively about 1 site to about 250 sites, or 25 sites to 200 site, or 50 sites to 150 sites.

Direct Synthesis of Dimethyl Ether from Syngas

Figure 2:
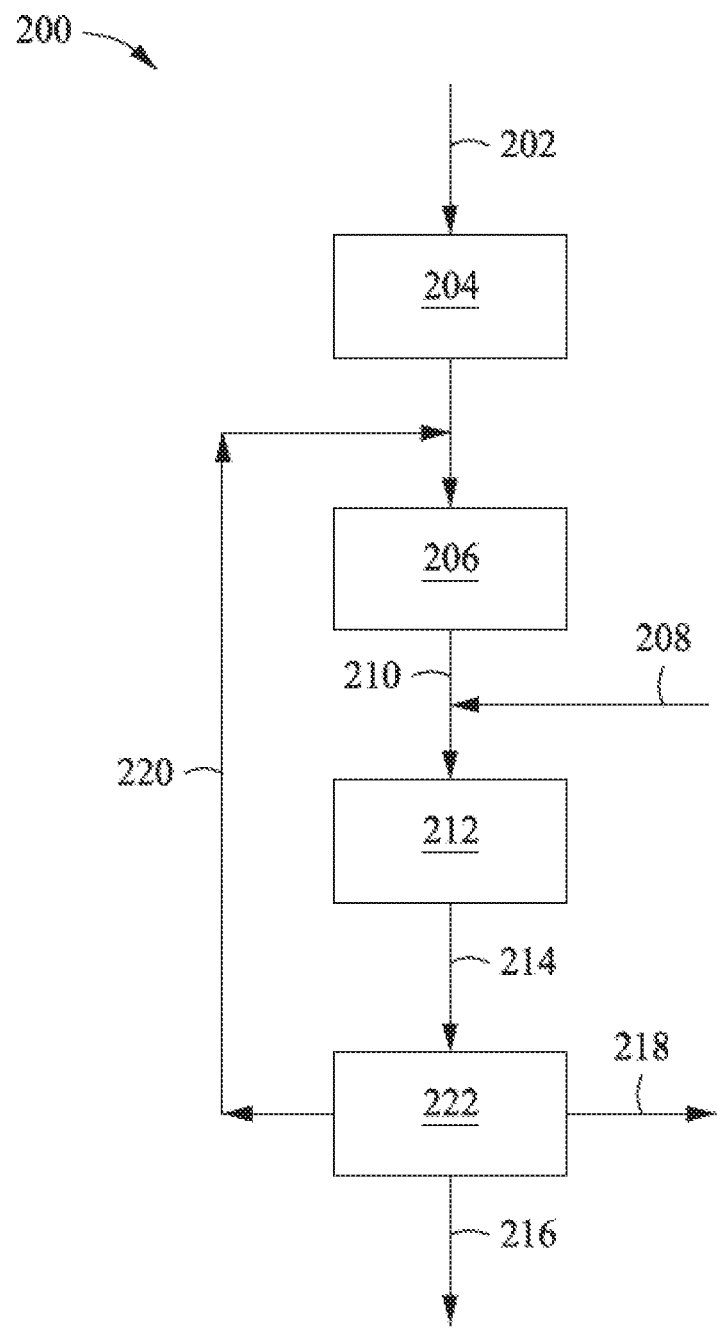
FIG. 2 is a flowchart illustrating an example integrated system and process for producing dimethyl ether from natural gas according to one or more embodiments of the present invention.

An example 200 method and system for the production of dimethyl ether from natural gas is illustrated in FIG. 2. A natural gas stream 202 is fed to a pretreater 204 to remove contaminants such as sulfur, chlorides and olefins. The pretreater 204 may be a single unit or, more likely, it is a series of units for removing the different types of contaminants found in the natural gas stream 204. For example, the pretreater 204 may include a desulfurizing column for removing sulfur. The pretreater 204 can also include a guard bed to remove chlorides and/or a hydrotreater to covert olefins to paraffins.

The pretreated natural gas may then be fed to a reformer 206, which may be a reverse flow reactor, to convert the natural gas to a syngas 210. A recycled $CO_2$ stream 220, which may also include recycled methane, can be fed with the treated natural gas to the reformer 206. It is noted that the pretreated natural gas stream may contain essentially zero $CO_2$ (such as the gas in pipeline gas) or it may have a high $CO_2$ content. Steam may also be added to the reformer 206 to promote the conversion of natural gas to syngas.

Steam 208 and syngas 210 are co-fed to a dimethyl ether reactor 212 to produce a product stream 214, which can include dimethyl ether, carbon dioxide, methane, hydrogen, and other byproducts. The dimethyl ether reactor 212 may operate a temperature of about 200° C. to about 300° C. (or about 230° C. to about 270° C.), a pressure of about 20 bar to about 50 bar (or about 30 bar to about 40 bar), and a gas hourly space velocity (GHSV) of about 1,000 $hr^{-1}$ to about 8,000 $hr^{-1}$ (or about 1,500 $hr^{-1}$ to about 3,000 $hr^{-1}$).

The product stream 214 may be fed to one or more separators 222 to separate the methane, carbon dioxide, and other byproducts 218 from dimethyl ether 216. Methane and carbon dioxide may be recycled back to the reformer 206 via the recycle stream 28. The separation of the products may be accomplished using various separation processes including refrigeration, distillation/fractionation, high-pressure or low-pressure flash separation, or membrane separation.

Prior to running the foregoing method, the acid/metal bifunctional catalyst system may be activated by exposure to hydrogen at elevated temperatures (e.g., about 150° C. to about 350° C., or about 200° C. to about 300° C.).

Direct dimethyl ether synthesis may be performed by converting syngas to methanol (Eq. 1) with the in-situ dehydration of methanol to dimethyl ether (Eq. 3). Advantageously, both reactions can occur in the same reactor such that the methanol is nearly instantaneously dehydrated to dimethyl ether as it is produced. In addition, a water gas shift reaction (Eq. 2) is typically present.

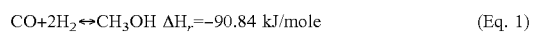

$$CO+2H_2 \leftrightarrow CH_3OH \quad \Delta H_r=-90.84 \text{ kJ/mole} \qquad (Eq.\ 1)$$

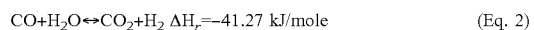

$$CO+H_2O \leftrightarrow CO_2+H_2 \quad \Delta H_r=-41.27 \text{ kJ/mole} \qquad (Eq.\ 2)$$

The equilibrium of the methanol reaction (Eq. 1) at high temperatures required to promote kinetics, is reactant favored and limits the overall syngas conversion in a traditional methanol process. However, the disclosed acid/metal bifunctional catalyst system may enable the in-situ dehydration of methanol immediately after it is formed, which maintains the system sufficiently far from equilibrium limitations of Eq. 1 and may improve the per-pass conversion of syngas.

Various by-products can also be produced during the conversion of syngas to methanol (e.g., methane, water, carbon dioxide, formic acid) and the conversion of methanol to dimethyl ether (e.g., acetates, hydrocarbons, methane, water, and coke). Acetates are known to facilitate metal sintering and metal ion-exchange on the acid catalyst that lead to catalyst deactivation.

Because the addition of steam reduces the per-pass selectivity to dimethyl ether by converting some carbon monoxide to carbon dioxide (Eq. 2), the amount of water present in the dimethyl ether reactor would conventionally be limited to the minimal amounts desired to mitigate coke formation. However, it has been found that the addition of steam in the proposed integrated process can be used to control production of $CO_2$ in the dimethyl ether reactor, which can improve the carbon efficiency of the system or process as described in further detail herein. Furthermore, surprisingly, it has been found that co-feeding steam in such quantities can reduce the selectivity towards hydrocarbons and oxygenates, thereby improving the acid/metal bifunctional catalyst system stability.

The total reaction of a system for the synthesis of dimethyl ether (Eq. 4) including the water-gas-shift reaction, methanol synthesis reaction, and dehydration reaction is exothermic.

$$2CH_3OH \leftrightarrow CH_3\!-\!O\!-\!CH_3 + H_2O \quad \Delta H_r = -21.26 \text{ kJ/mole} \quad \text{(Eq. 3)}$$

$$3CO + 3H_2 \leftrightarrow CH_3\!-\!O\!-\!CH_3 + CO_2 \quad \Delta H_r = -246 \text{ kJ/mole} \quad \text{(Eq. 4)}$$

It has been found that carbon efficiency can be improved by controlling feed parameters, particularly the amount of water added to either the reforming reactor or the dimethyl ether reactor. Conventionally, syngas conversion process use factors like $H_2$:CO ratio or M-value, which is $(H_2-CO_2)/(CO+CO_2)$, to define the ideal feed to the syngas conversion reactor. The numerical value selected for this metric typically reflects the ideal stoichiometry for the desired product reaction. Additionally, the presence of water is typically ignored or treated like an inert.

Water, however, plays a critical role in the integrated process described herein. Water may be added in amount to leverage the water-gas-shift reaction to co-produce $CO_2$ (as needed to maximize carbon efficiency) in the dimethyl ether reactor. The amount of water added, is a function of the syngas composition (namely the amount of $CO/CO_2/H_2/H_2O$ present in the feed to the dimethyl ether reactor), which is a function of the steam reforming relative to the dry reforming carried out in the syngas reactor.

A preferred feed to the dimethyl ether reactor may be described with a modified M value (Mm) per the following equation.

$$Mm = \frac{H_2 - CO_2 + H_2O}{CO + CO_2 - H_2O}$$

Water may be added to the process in total, either in the syngas reactor for steam reforming or in the dimethyl ether reactor. Independent of how the water is split between the reactors this corresponds to a modified M-value of about 1.4 to 1.8 (or 1.5 to 1.7, or 1.6).

Various reforming processes may be employed to produce syngas from such a natural gas feedstream including, but not limited to, partial oxidation, steam methane reforming, autothermal reforming, dry reforming, and the like, and any combination thereof. Preferably, the natural gas stream is reformed using a reverse flow reactor.

Any natural gas feedstream can be reformed into syngas. As used herein, "natural gas" refers to a hydrocarbon feed that is predominantly $C_1$ to $C_4$ hydrocarbons, and it may be predominantly methane. The natural gas feedstream can also include carbon dioxide. For simplicity, examples used herein may make specific reference to methane; however, it should be understood that natural gas feed streams further comprising $C_2$-$C_4$ hydrocarbons may also be used. General equations for the dry reforming and steam reforming for such hydrocarbons are shown in Eq. 5 and Eq. 6, respectively.

$$C_nH_{2n+1}CO_2 \rightarrow 2nCO + (n+1)H_2 \quad \text{(Eq. 5)}$$

$$C_nH_{2n+1} + H_2O \rightarrow nCO + (2n+1)H_2 \quad \text{(Eq. 6)}$$

In order to improve carbon efficiency of the system, it is desirable to provide a feed of natural gas and carbon dioxide to the reverse flow reactor at a natural gas:carbon dioxide molar ratio of about 1:1, such as about 0.8:1 to about 1.1:1. For example, 2 moles of $CO_2$ and 2 moles of methane may produce 4 moles of CO and 4 mole of $H_2$ as shown in Eq. 7.

$$2CO_2 + 2CH_4 \leftrightarrow 4CO + 4H_2 \quad \text{(Eq. 7)}$$

If the products of Eq. 5 were then fed to the dimethyl ether reactor with steam as a co-feed, the following products would be produced: 1 mole of dimethyl ether, 2 moles of $CO_2$ and 1 mole of $H_2$ (Eqs. 4 and 2).

The reverse flow reactor for reforming the natural gas to syngas may operate at a temperature of about 300° C. and about 1400° C. (or about 500° C. and about 1000° C.) and a pressure range of about 1 bar and about 100 bar (or about 10 bar to about 50 bar).

The effluent from the dimethyl ether reactor may be separated into dimethyl ether, $CO_2$ (optionally with any unreacted $CH_4$, CO, and/or $H_2$), and other byproducts. Any one or combination of separation processes may be employed to perform such separations including, but not limited to, refrigeration, distillation/fractionation, flash separation and membrane separation. The $CO_2$, $CH_4$, and any unreacted intermediates may be recycled as described herein.

Advantageously, recycle streams having desirable compositions can be obtained from separation processes downstream of the dimethyl ether reactor. These recycle streams can be used to improve the carbon efficiency of the integrated system and/or can provide other advantages.

In any embodiment, $CO_2$ and $CH_4$, and optionally CO, recovered downstream of dimethyl ether reactor may be recycled upstream of the syngas generation reactor. The $CO_2$ may be provided in sufficient quantities such that when added to the $CO_2$ native to the natural gas feed will achieve the desired natural gas:carbon dioxide ratio, such as a methane:carbon dioxide molar ratio of about 1:1, such as about 0.9:1.1 to about 1.1:0.9. In some cases, it may be desirable to recycle at least a portion of the $CO_2$ and $CH_4$, and optionally CO and methanol, upstream of the dimethyl ether reactor but downstream of the syngas generator reactor.

Hydrogen may also be recovered from the separation processes and used as fuel. Optionally, at least a portion of the hydrogen can be recycled upstream of the dimethyl ether reactor.

EXAMPLE EMBODIMENTS

A first nonlimiting embodiment of the present disclosure is a method comprising: mixing two or more metal salts and an aluminum salt in water to produce a metal catalyst precursor solution; mixing the metal catalyst precursor solution and an alkali metal buffer solution to produce a precipitate; ion exchanging the alkali metal in the precipitate for a non-alkali cation to produce a low-alkali metal precipitate comprising 3 wt % or less alkali metal by weight of the precipitate on a dry basis; producing a powder from the low-alkali metal precipitate; and calcining the powder to produce a metal catalyst. Optionally, this embodiment can further include one or more of the following: Element 1: wherein ion exchanging comprises contacting the precipitate with the non-alkali cation; Element 2: wherein ion exchanging comprises dialysis; Element 3: wherein ion exchanging comprises electrochemical ion exchange; Element 4: wherein producing the powder from the low-alkali metal precipitate comprises: washing the low-alkali metal precipitate; drying the low-alkali metal precipitate; and grinding the low-alkali metal precipitate, wherein the powder comprises 5 wt % or less of the water; Element 5: wherein the alkali metal buffer solution is at 40° C. to 90° C. when mixing with the metal catalyst precursor solution; Element 6: wherein ion exchanging is performed at 40° C. to 90° C.; Element 7: wherein the non-alkali cation is ammonium or hydrogen; Element 8: wherein the two or more metal salts comprise a first metal salt that is a salt of a first metal selected from the group consisting of Cu, Cr, Ag, Au, Ru, Rh, Pd, Re, Os, Ir, and Pt and a second metal salt that is a salt of a second metal selected from the group consisting of Ti, V, Cr, Mn, Fe, Co, Ni, Zn, a rare earth metal, a La series metal, and a Y series metal; Element 9: Element 8 and wherein two or more first metal catalysts are included in the metal catalyst precursor solution; Element 10: Element 8 and wherein two or more second metal catalysts are included in the metal catalyst precursor solution; Element 11: wherein the metal catalyst is a M1/M2/Al catalyst, wherein M1 is selected from the group consisting of Cu, Cr, Ag, Au, Ru, Rh, Pd, Re, Os, Ir, Pt, and any combination thereof, wherein M2 is selected from the group consisting of Ti, V, Cr, Mn, Fe, Co, Ni, Zn, a rare earth metal, a La series metal, a Y series metal, and any combination thereof, and wherein M1 and M2 are different; Element 12: wherein calcining is performed in air at 200° C. to 400° C.; Element 13: wherein the metal catalyst has an average diameter of 0.01 μm to 10 μm; Element 14: wherein the metal catalyst has a $N_2$ BET surface area according to ASTM D3663-03 (2015) of about 40 m²/g to about 200 m²/g; Element 15: wherein the metal catalyst has an average pore volume according to about 0.1 mL/g to about 1.2 mL/g; Element 16: wherein the metal catalyst has an average pore size according to ASTM D4641-17 of about 5 nm to about 25 nm; Element 17: the method further comprising: mixing the metal catalyst with an acid catalyst to produce an acid/metal bifunctional catalyst system; Element 18: Element 17 and wherein the acid catalyst is selected from the group consisting of a zeolite, an ion exchanged zeolite, a molecular sieve, a metal oxide, and any combination thereof; Element 19: Element 17 and wherein the acid catalyst is present at 10 wt % to 80 wt % relative to the total catalyst weight in the acid/metal bifunctional catalyst system; Element 20: Element 17 and wherein the acid catalyst is present at 10 wt % to 50 wt % relative to the total catalyst weight in the acid/metal bifunctional catalyst system; Element 21: Element 17 and wherein the mixing step comprises: dry mixing the carbon-coated metal catalyst particle with an acid catalyst to produce the acid/metal bifunctional catalyst system; Element 22: Element 17 and wherein the mixing step comprises: mixing the carbon-coated metal catalyst particle with an acid catalyst and a binder to form a dough; and extruding the dough to produce the acid/metal bifunctional catalyst system; Element 23: Element 17 and wherein the mixing step comprises: mixing the carbon-coated metal catalyst particle with an acid catalyst and a solvent to form a slurry; heating the slurry; and drying the slurry to produce the acid/metal bifunctional catalyst system; Element 24: Element 17 and the method further comprising: activating the acid/metal bifunctional catalyst system in the presence of hydrogen at 150° C. to 350° C.; and reacting the activated acid/metal bifunctional catalyst system with a feedstream comprising hydrogen and carbon monoxide; Element 25: Element 24 and wherein reacting is at a temperature of about 200° C. to about 300° C., a pressure of about 20 bar to about 50 bar, and a gas hourly space velocity (GHSV) of about 1,000 $hr^{-1}$ to about 8,000 $hr^{-1}$; and Element 26: Element 24 and wherein the reacting the activated acid/metal bifunctional catalyst system with the feedstream is in the presence of steam. Examples of combinations include, but are not limited to, two or more of Elements 1-3 in combination; one or more of Elements 1-3 in combination with one or more of Elements 4-10; one or more of Elements 1-10 in combination with one or more of Elements 11-16; two or more of Elements 13-16 in combination; one or more of Elements 1-16 in combination with Element 17 and optionally in further combination with one or more of Elements 18-26; Element 17 in combination with one of Elements 21-23; Elements 17 and 18 in combination and optionally in further combination with one or both of Elements 18 and 19; and Element 17 in combination with one or more of Elements 24-26 and optionally in further combination with one or more of Elements 18-23.

A second nonlimiting example embodiment is an acid/metal bifunctional catalyst system comprising the metal catalyst of the first nonlimiting example embodiment optionally further characterized by one or more of Elements 11, 13, 14, 15, or 16.

A third nonlimiting example embodiment is a metal catalyst produced according to the first nonlimiting example embodiment optionally further including or characterized by one or more of Elements 1-16.

A fourth nonlimiting example embodiment is an acid/metal bifunctional catalyst system produced according the first nonlimiting example embodiment with Element 17 and optionally further including or characterized by one or more of remaining of Elements 1-26.

Unless otherwise indicated, all numbers expressing quantities of ingredients, properties such as molecular weight, reaction conditions, and so forth used in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the embodiments of the present invention. At the very least, and not as an attempt to limit the application of the doctrine of equivalents to the scope of the claim, each numerical parameter should at least be construed in light of the number of reported significant digits and by applying ordinary rounding techniques.

One or more illustrative embodiments incorporating the invention embodiments disclosed herein are presented herein. Not all features of a physical implementation are described or shown in this application for the sake of clarity.

It is understood that in the development of a physical embodiment incorporating the embodiments of the present invention, numerous implementation-specific decisions must be made to achieve the developer's goals, such as compliance with system-related, business-related, government-related and other constraints, which vary by implementation and from time to time. While a developer's efforts might be time-consuming, such efforts would be, nevertheless, a routine undertaking for those of ordinary skill in the art and having benefit of this disclosure.

While compositions and methods are described herein in terms of "comprising" various components or steps, the compositions and methods can also "consist essentially of" or "consist of" the various components and steps.

To facilitate a better understanding of the embodiments of the present invention, the following examples of preferred or representative embodiments are given. In no way should the following examples be read to limit, or to define, the scope of the invention.

EXAMPLES

Preparation of 60% CuO/30% ZnO/10% $Al_2O_3$
(Sample 1)

Solution A was prepared by dissolving 27.337 g of cupric nitrate trihydrate, 16.452 g of zinc nitrate hexahydrate, and 11.037 g of aluminum nitrate nonahydrate in 300 g of deionized $H_2O$. Solution B was 1000 mL of 1.0 M solution of $KH_2PO_4$—$K_2HPO_4$ (pH 7.4), purchased from Aldrich. Solution B was heated in a water-bath with temperature maintained at 70° C. With magnetic stirring, Solution A was slowly added into Solution B. When 300 mL of Solution A was added into Solution B, the pH of the mixture solution was decreased to 7.0 from the initial pH of 7.4. While maintaining the temperature of the slurry at 70° C., the mixture slurry was aged for 1 hour. The power of water bath was turned off and the mixture slurry was cooled down to room temperature. A slurry cake was recovered by filtration. The wet cake was washed with distilled water thoroughly. The sample was dried at 120° C. in air for 16 hours.

The dried sample was then ground to reduce the particle size. After grinding, the sample was placed in a box furnace. The furnace was ramped from room temperature to 300° C. at rate of 10° F./min (5.6° C./min) in air. The air flowing rate is set at 5 volume/volume catalyst/minute. The samples were held at 300° C. in air for 3 hrs.

Preparation of 60% CuO/30% ZnO/10% $Al_2O_3$
(Sample 2)

In order to reduce alkali metal content in Sample 1, 10 g of Sample 1 was ion-exchanged with 300 mL of 1 N (normal) ammonium nitrate solution at room temperature for 4 hrs. The slurry cake was recovered by filtration. The wet cake was washed with 300 mL of distilled water two times. Then, the sample was ion exchanged again with fresh 300 mL of 1 N ammonium nitrate solution at room temperature for 4 hrs. The slurry cake was recovered by filtration. The wet cake was washed with 300 mL of distilled water twice. The sample was dried at 120° C. in air for 16 hours. After grinding, the sample was placed in a box furnace. The furnace was ramped from room temperature to 300° C. at rate of 10° F./min (5.6° C./min) in air. The air flowing rate is set at 5 volume/volume catalyst/minute. The samples were held at 300° C. in air for 3 hrs.

Preparation of 60% CuO/30% ZnO/10% $Al_2O_3$
(Sample 3)

To further reduce alkali metal K content in Sample 1, 10 g of Sample 1 was ion-exchanged with 300 mL of 1 N ammonium nitrate solution at 80° C. for 4 hrs. The slurry cake was recovered by filtration. The wet cake was washed with 300 mL of distilled water two times. Then, the sample was ion exchanged again with fresh 300 mL of 1 N ammonium nitrate solution at 80° C. for 4 hrs. The slurry cake was recovered by filtration. The wet cake was washed with 300 mL of distilled water twice. The sample was dried at 120° C. in air for 16 hours. After grinding, the sample was placed in a box furnace. The furnace was ramped from room temperature to 300° C. at rate of 10° F./min (5.6° C./min) in air. The air flowing rate is set at 5 volume/volume catalyst/minute. The samples were held at 300° C. in air for 3 hrs.

Catalysts Properties

Figure 3:
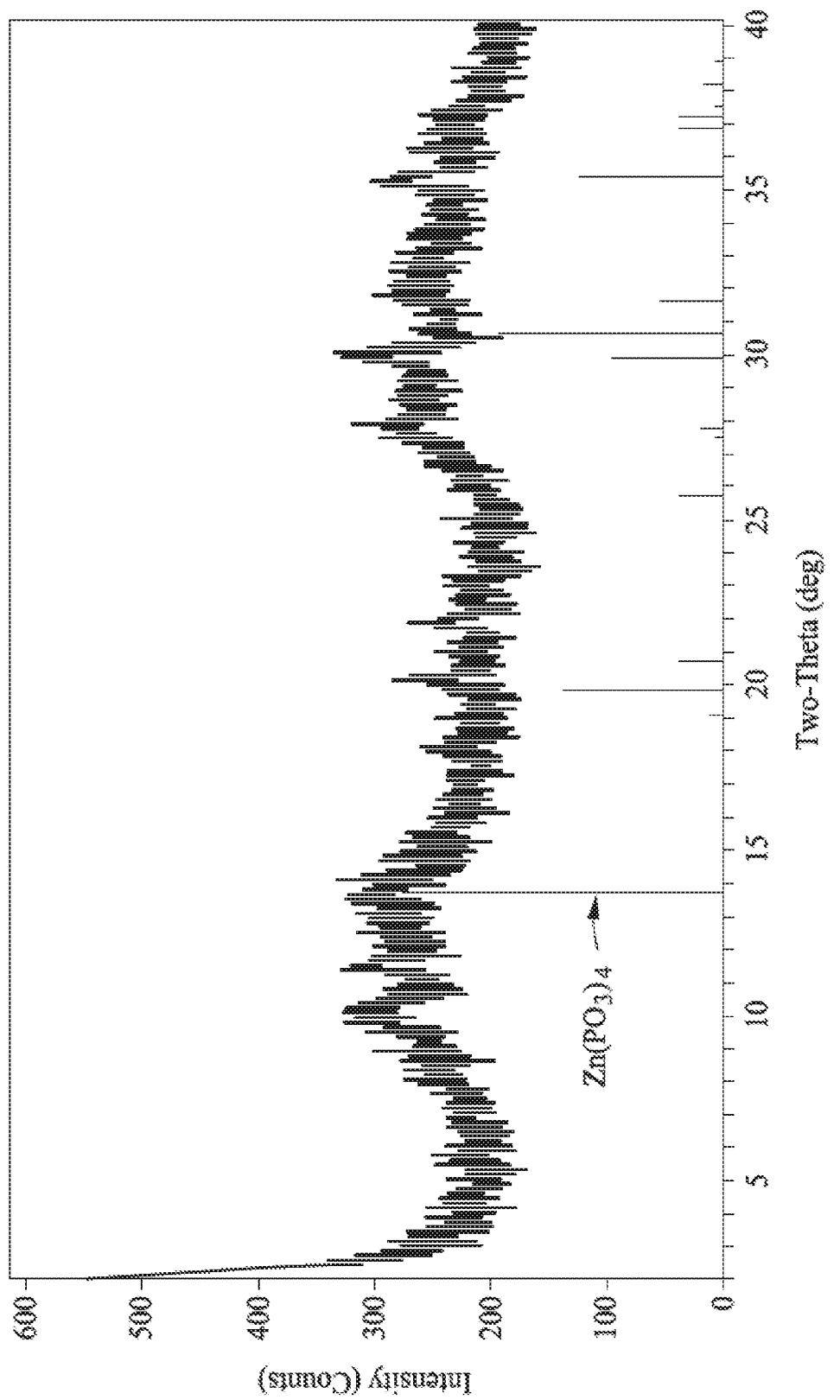
FIG. 3 illustrates the x-ray diffraction (XRD) patterns of a metal catalyst.

Sample 1 CuZnAl catalyst has $N_2$ BET surface area of 59 $m^2/g$, pore volume of 0.23 mL/g, and pore size of 17.0 nm. XRD pattern of bulk CuZnAl Sample 1 is shown in FIG. 3 illustrating that Sample 1 is amorphous in nature. It only has very broad XRD peaks identified as zinc phosphate, which is very poorly crystallized. Inter-formation of the hydroxides or phosphates of Cu, Al, and Zn by co-precipitations of nitrates of Cu, Al, and Zn with phosphate buffer solution may interrupt the crystallizations of hydroxides of Cu, Zn, and Al. Upon calcination, crystallites of oxides of Cu, Zn, and Al are either amorphous or too small to be detected by XRD. Upon catalyst activation (reduction), Cu metal is highly dispersed on the surfaces of Zn and Al oxides.

Table 1 shows the compositions of CuZnAl samples measured by X-Ray Fluorescence (XRF). Sample 1, Sample 2, and Sample 3 contain similar amount of Al, 2.45%, 2.99%, and 2.84%, respectively. They also have similar amount of Cu, P and Zn as listed in Table 1. Sample 1 contains substantial amount of K, 4.03 wt %. After ion-exchanging with 1N ammonium nitrate solution at room temperature, the K content in Sample 2 was reduced to 3.18 wt %. After ion-exchanging at 80° C., the K content in Sample 3 was further reduced to 1.40 wt %. Higher ion exchanging temperature is more efficient for the reduction of K content in the CuZnAl metal catalysts.

TABLE 1

| Sample | wt % Al | wt % P | wt % Cu | wt % Zn | wt % K |
|---|---|---|---|---|---|
| 1 | 2.45 | 16.69 | 28.18 | 13.29 | 4.03 |
| 2 | 2.99 | 16.02 | 29.39 | 13.50 | 3.18 |
| 3 | 2.84 | 16.33 | 30.21 | 14.18 | 1.40 |

Catalyst Testing

Four catalyst systems were prepared by mixing a reference metal catalyst commercially available CuZnAl catalyst, Sample 1, Sample 2, or Sample 3 with CATAPAL® $Al_2O_3$ with in amounts 50 wt % metal catalyst to 50 wt % acid catalyst. In separate reactions, a reactor was charged with each of the four catalyst systems with 125 μm to 160 μm α-$Al_2O_3$ particles above and below the catalysts bed. The catalysts in the reactor were activated by flowing hydrogen at 250° C. over the catalyst bed for 120 minutes. Then, the catalysts were used in a syngas to dimethyl ether reaction under the following conditions: a temperature of 230° C. to 270° C., a pressure of 25 bar to 50 bar, and a gas hourly space velocity (GHSV) of 1,000 $hr^{-1}$ to 8,000 $hr^{-1}$. The reaction feed was 37 vol % to 50 vol % $H_2$, 40 vol % to 50 vol % CO, 13 vol % to 40 vol % $CO_2$, 0 vol % to 3 vol % $CH_4$, 5 vol % to 10 vol % Ar (used as an internal standard), and 0 vol % to 10 vol % of $H_2O$. A gas chromatograph fitted with a flame-ionization detector (FID), a thermal conductivity detector (TCD), and optionally a helium ionization detector (HID) (for low water concentrations of 200 ppm to 2 vol %) was used to analyze the product stream.

Figure 4:
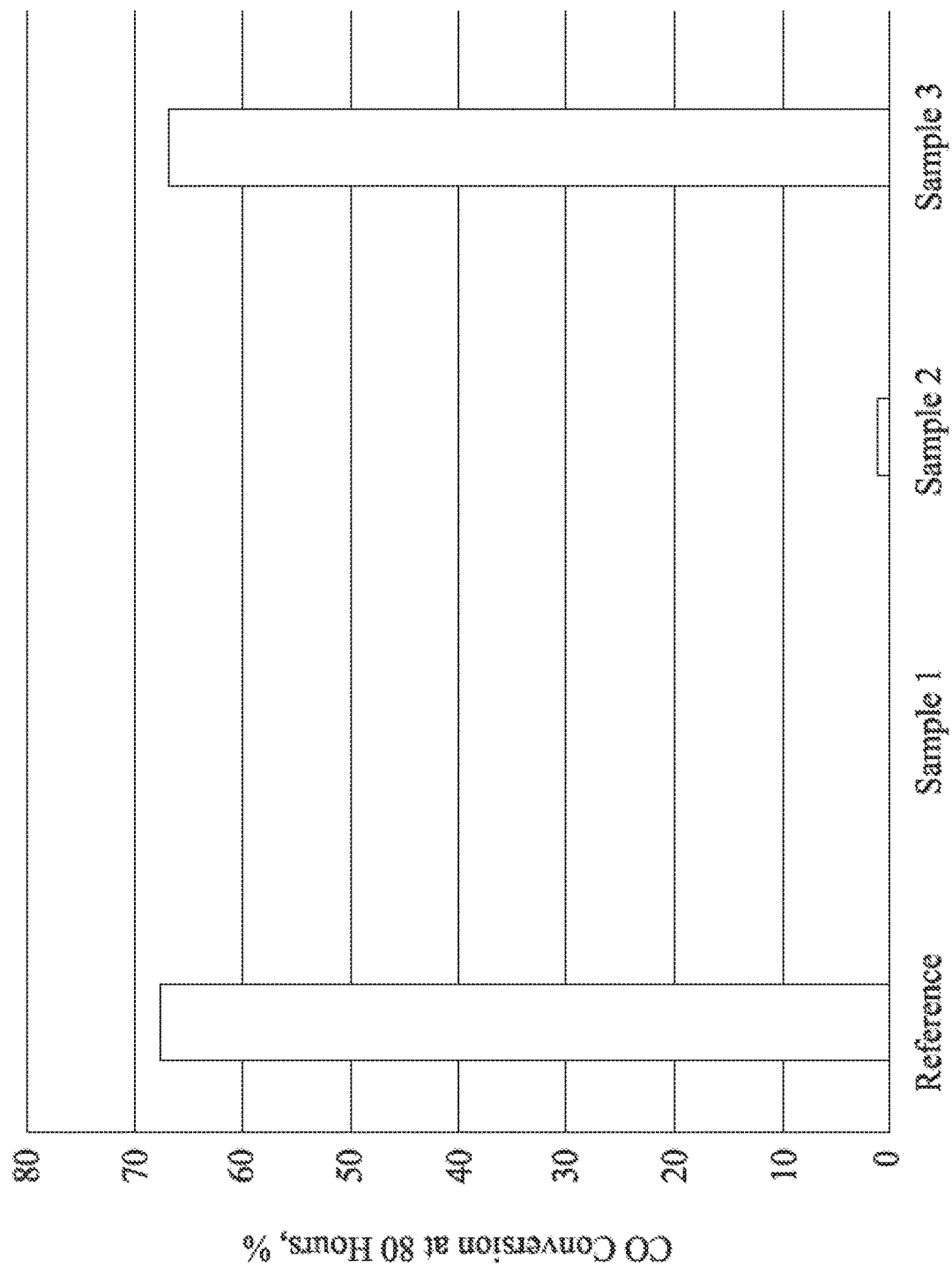
FIG. 4 is a plot of the CO conversion for each of the acid/metal bifunctional catalyst systems based on the Reference and Samples 1-3.

FIG. 4 is a plot of the CO conversion for each of the four catalyst systems after 80 hours of the catalyst beds being exposed to the reaction feed. At 250° C., 35 bar pressure, and GHSV of 2100 $hr^{-1}$, the CO conversion activity of the Reference-based catalyst system reached a steady state, around 68%. Sample 1-based and Sample 2-based catalyst systems have no CO conversion activities. The CO conversion activity results are consistent with the XRF data. Sample 1 contains a substantial amount of K, 4.03 wt %, which completely shuts down its methanol synthesis activity. After ion-exchanging with ammonium nitrate solution at room temperature, the K content in Sample 2 was reduced to 3.18 wt %. The Sample 2-based catalyst system started to show very low CO conversion activity, less than 1%. After ammonium nitrate solution ion-exchanging at 80° C., the K content in Sample 3 was reduced to 1.40 wt %. The CO conversion activity of Sample 3-based catalyst system is close to that of the reference catalyst, around 67%. Therefore, CO conversion activities of CuZnAl samples strongly depend on residual alkali metal K concentration in the catalyst.

Figure 5:
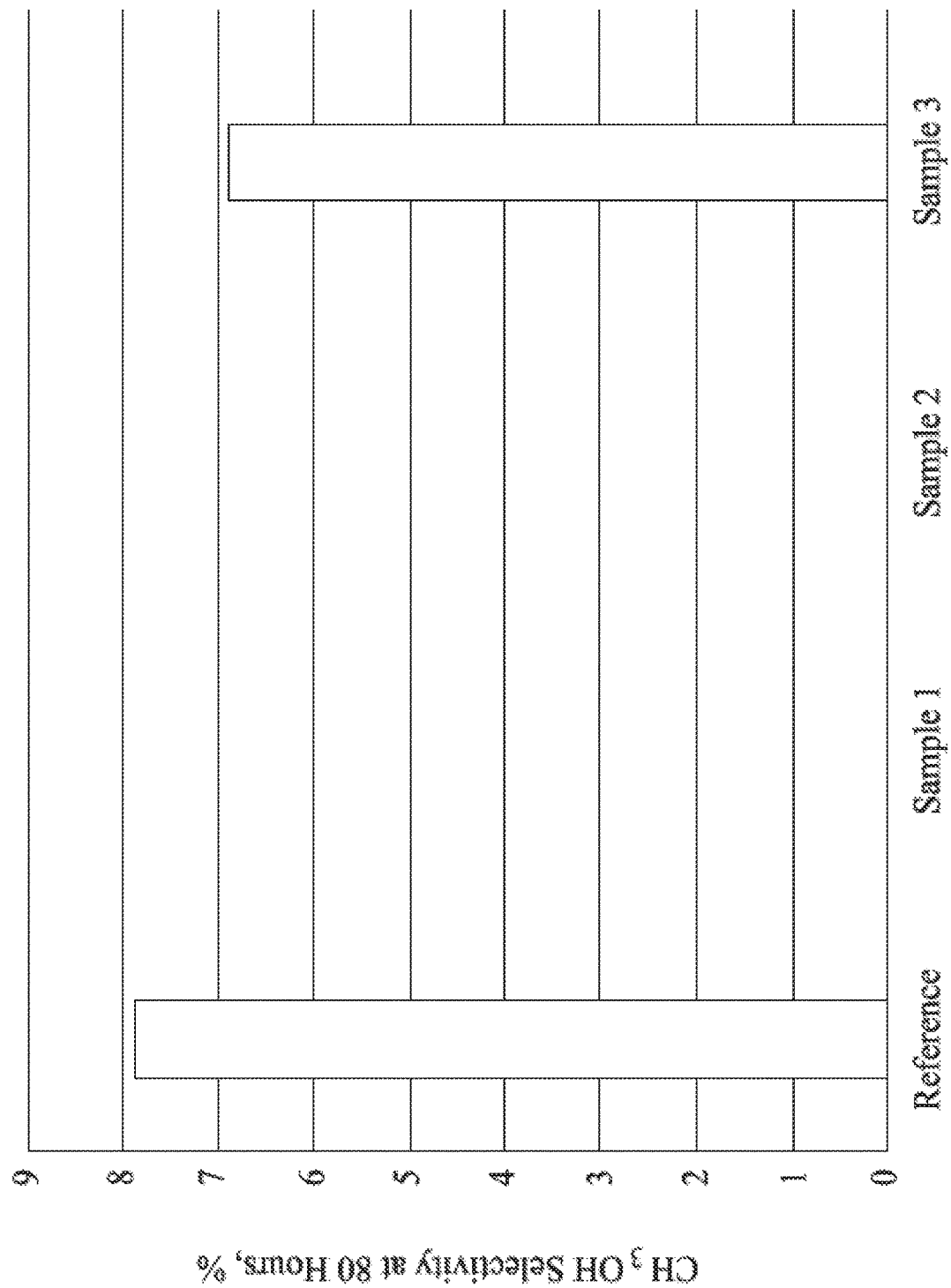
FIG. 5 is a plot of methanol selectivity for each of the acid/metal bifunctional catalyst systems based on the Reference and Samples 1-3.

FIG. 5 is a plot of methanol selectivity for each of the four catalyst systems after 80 hours of the catalyst beds being exposed to the reaction fee. Since all four samples include the same acid catalyst, the dehydration activities in catalyst systems should be the same, or very close to each other. Therefore, the methanol selectivity is linked to the methanol synthesis activity. The Reference-based catalyst system has ~8% methanol selectivity, and the Sample 3-based catalyst system has comparable methanol selectivity around 7%. Sample 1-based catalyst system and Sample 2-based catalyst system have no methanol selectivites, which are consistent with no CO conversions observed in the Sample 1-based catalyst system and Sample 2-based catalyst system.

Figure 6:
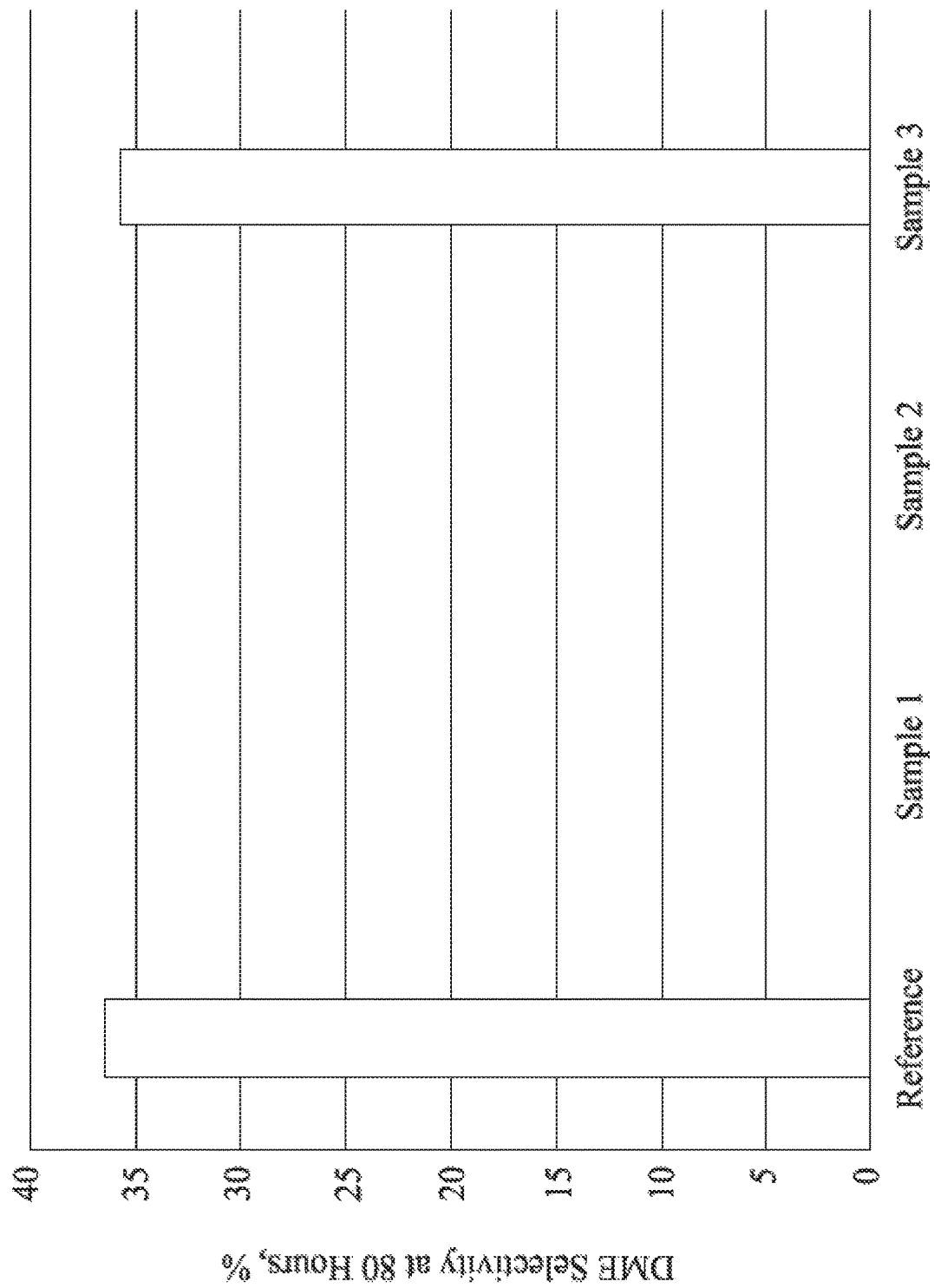
FIG. 6 is a plot of the dimethyl ether selectivity for each of the acid/metal bifunctional catalyst systems based on the Reference and Samples 1-3.

FIG. 6 is a plot of the dimethyl ether (DME) selectivity for each of the four catalyst systems after 80 hours of the catalyst beds being exposed to the reaction feed. The dimethyl ether selectivity of Reference-based catalyst system is 36.5%. Sample 3-based catalyst system has comparable dimethyl ether selectivity around 35.7%. Sample 1-based catalyst system and Sample 2-based catalyst system have no dimethyl ether selectivites because there were no CO conversions on these two metal catalysts due to high K metal contents inside catalysts.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present invention. The invention illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces.

The invention claimed is:

1. A method comprising:
   mixing two or more metal salts and an aluminum salt in water to produce a metal catalyst precursor solution;
   mixing the metal catalyst precursor solution and an alkali metal buffer solution to produce a precipitate;
   ion exchanging the alkali metal in the precipitate for a non-alkali cation to produce a low-alkali metal precipitate comprising 3 wt % or less alkali metal by weight of the precipitate on a dry basis;
   producing a powder from the low-alkali metal precipitate; and
   calcining the powder to produce a metal catalyst.

2. The method of claim 1, wherein ion exchanging comprises contacting the precipitate with the non-alkali cation.

3. The method of claim 1, wherein ion exchanging comprises dialysis.

4. The method of claim 1, wherein ion exchanging comprises electrochemical ion exchange.

5. The method of claim 1, wherein producing the powder from the low-alkali metal precipitate comprises:
   washing the low-alkali metal precipitate;
   drying the low-alkali metal precipitate; and
   grinding the low-alkali metal precipitate, wherein the powder comprises 5 wt % or less of the water.

6. The method of claim 1, wherein the alkali metal buffer solution is at 40° C. to 90° C. when mixing with the metal catalyst precursor solution.

7. The method of claim 1, wherein ion exchanging is performed at 40° C. to 90° C.

8. The method of claim 1, wherein the non-alkali cation is ammonium or hydrogen.

9. The method of claim 1, wherein the two or more metal salts comprise a first metal salt that is a salt of a first metal selected from the group consisting of Cu, Cr, Ag, Au, Ru, Rh, Pd, Re, Os, Ir, and Pt and a second metal salt that is a salt of a second metal selected from the group consisting of Ti, V, Cr, Mn, Fe, Co, Ni, Zn, a rare earth metal, a La series metal, and a Y series metal.

10. The method of claim 9, wherein two or more first metal catalysts are included in the metal catalyst precursor solution.

11. The method of claim 9, wherein two or more second metal catalysts are included in the metal catalyst precursor solution.

12. The method of claim 1, wherein the metal catalyst is a M1/M2/Al catalyst, wherein M1 is selected from the group consisting of Cu, Cr, Ag, Au, Ru, Rh, Pd, Re, Os, Ir, Pt, and any combination thereof, wherein M2 is selected from the group consisting of Ti, V, Cr, Mn, Fe, Co, Ni, Zn, a rare earth metal, a La series metal, a Y series metal, and any combination thereof, and wherein M1 and M2 are different.

13. The method of claim 1, wherein calcining is performed in air at 200° C. to 400° C.

14. The method of claim 1, wherein the metal catalyst has an average diameter of 0.01 μm to 10 μm.

15. The method of claim 1, wherein the metal catalyst has a $N_2$ BET surface area according to ASTM D3663-03 (2015) of about 40 $m^2/g$ to about 200 $m^2/g$.

16. The method of claim 1, wherein the metal catalyst has an average pore volume according to about 0.1 mL/g to about 1.2 mL/g.

17. The method of claim 1, wherein the metal catalyst has an average pore size according to ASTM D4641-17 of about 5 nm to about 25 nm.

18. The method of claim 1 further comprising:
mixing the metal catalyst with an acid catalyst to produce an acid/metal bifunctional catalyst system.

19. The method of claim 18, wherein the acid catalyst is selected from the group consisting of a zeolite, an ion exchanged zeolite, a molecular sieve, a metal oxide, and any combination thereof.

20. The method of claim 18, wherein the acid catalyst is present at 10 wt % to 80 wt % relative to the total catalyst weight in the acid/metal bifunctional catalyst system.

21. The method of claim 18, wherein the acid catalyst is present at 10 wt % to 50 wt % relative to the total catalyst weight in the acid/metal bifunctional catalyst system.

22. The method of claim 18, wherein the mixing step comprises:
dry mixing the metal catalyst with an acid catalyst to produce the acid/metal bifunctional catalyst system.

23. The method of claim 18, wherein the mixing step comprises:
mixing the metal catalyst with an acid catalyst and a binder to form a dough; and
extruding the dough to produce the acid/metal bifunctional catalyst system.

24. The method of claim 18, wherein the mixing step comprises:
mixing the metal catalyst with an acid catalyst and a solvent to form a slurry;
heating the slurry; and
drying the slurry to produce the acid/metal bifunctional catalyst system.

25. The method of claim 18 further comprising:
activating the acid/metal bifunctional catalyst system in the presence of hydrogen at 150° C. to 350° C.; and
reacting the activated acid/metal bifunctional catalyst system with a feedstream comprising hydrogen and carbon monoxide.

26. The method of claim 25, wherein reacting is at a temperature of about 200° C. to about 300° C., a pressure of about 20 bar to about 50 bar, and a gas hourly space velocity (GHSV) of about 1,000 $hr^{-1}$ to about 8,000 $hr^{-1}$.

27. The method of claim 25, wherein the reacting the activated acid/metal bifunctional catalyst system with the feedstream is in the presence of steam.

* * * * *